United States Patent
JinKim

(10) Patent No.: US 6,278,756 B1
(45) Date of Patent: Aug. 21, 2001

(54) ELECTROCHEMICAL CORROSION POTENTIAL SENSOR WITH INCREASED LIFETIME

(75) Inventor: Young JinKim, Clifton Park, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/708,110

(22) Filed: Nov. 6, 2000

Related U.S. Application Data

(62) Division of application No. 09/257,258, filed on Jul. 20, 1999, now Pat. No. 6,181,760.

(51) Int. Cl.⁷ .................... G21C 17/00; G01F 1/64; G01N 17/04; C25B 11/02; C25C 7/02
(52) U.S. Cl. ............. 376/245; 376/305; 205/775.5; 204/286; 204/404; 324/446; 324/700; 324/71.2; 324/439; 324/724
(58) Field of Search ................... 376/245, 249, 376/305; 205/775.5, 794.5; 204/280, 286, 404; 324/446, 700, 71.2, 439, 724

(56) References Cited

U.S. PATENT DOCUMENTS

| 4,636,292 | * | 1/1987 | Fejes et al. | 204/404 |
| 5,217,596 | * | 6/1993 | Indig et al. | 204/435 |
| 5,465,278 | * | 11/1995 | Cowan, II et al. | 376/245 |
| 5,465,281 | | 11/1995 | Andresen et al. | 376/305 |
| 5,571,394 | * | 11/1996 | Hettiarachchi et al. | 204/400 |
| 5,848,113 | | 12/1998 | Kim et al. | 376/305 |
| 5,896,432 | | 4/1999 | Kim et al. | 376/305 |

* cited by examiner

*Primary Examiner*—Charles T. Jordan
*Assistant Examiner*—Kyongtaek K. Mun
(74) *Attorney, Agent, or Firm*—Noreen C. Johnson; Douglas E. Stoner

(57) ABSTRACT

The invention relates to a sensor for a measuring an electrochemical corrosion potential comprising a sensor tip, a conductor electrically connected to the sensor tip, an insulating member which surrounds the conductor, a connecting member which surrounds the conductor; and a sleeve which fits over the sensor tip, the insulating member, and the connecting member, the sleeve having inner threads which engage with corresponding outer threads on at least one of the sensor tip and the connecting member.

4 Claims, 2 Drawing Sheets

ELECTROCHEMICAL CORROSION POTENTIAL SENSOR WITH INCREASED LIFETIME

This application is a division of application Ser. No. 09/257,258 filed Jul. 20, 1999, now U.S. Pat. No. 6,181,760.

FIELD OF THE INVENTION

The present invention relates generally to nuclear reactors, and more particularly to an electrochemical corrosion potential sensor for sensing the electrochemical corrosion potential of materials exposed to high temperature water.

BACKGROUND

A nuclear power plant includes a nuclear reactor for heating water to generate steam which is routed to a steam turbine. The steam turbine extracts energy from the steam to power an electrical generator which produces electrical power. The nuclear reactor is typically in the form of a boiling water reactor having nuclear fuel disposed in a reactor pressure vessel in which water is heated.

The water and steam are carried through various components and piping which are typically formed of stainless steel, with other materials such as iron based alloys and nickel based alloys being used for various components inside the reactor pressure vessel.

It has been found that these materials tend to undergo intergranular stress corrosion cracking depending on the chemistry of the material, the degree of sensitization, the presence of tensile stress, and the chemistry of the reactor water. By controlling one or more of these critical factors, it is possible to control the propensity of a material to undergo intergranular stress corrosion cracking.

However, it is conventionally known that intergranular stress corrosion cracking may be controlled or mitigated by controlling a single critical parameter called the electrochemical corrosion potential (ECP) of the material. Thus, considerable efforts have been made in the past decade to measure the electrochemical corrosion potential of the materials of interest during operation of the reactor. This measurement, however, is not a trivial task, because the electrochemical corrosion potential of the material varies depending on the location of the material in the reactor circuit.

As an example, a material in the reactor core region is likely to be more susceptible to radiation assisted stress corrosion cracking than the same material exposed to an out-of-core region. The increased susceptibility occurs because the material in the core region is exposed to the highly oxidizing species generated by the radiolysis of water by both gamma and neutron radiation under normal water chemistry conditions in addition to the effect of direct radiation assisted stress corrosion cracking. The oxidizing species increase the electrochemical corrosion potential of the material, which in turn increases its propensity to undergo intergranular stress corrosion cracking or radiation assisted stress corrosion cracking.

Thus, a suppression of the oxidizing species is desirable in controlling intergranular stress corrosion cracking. An effective method of suppressing the oxidizing species coming into contact with the material involves the injection of hydrogen into the reactor water via the feedwater system so that recombination of the oxidants with hydrogen occurs within the reactor circuit. The recombination results in an overall reduction in the oxidant concentration present in the reactor which in turn mitigates intergranular stress corrosion cracking of the materials if the oxidant concentration is suppressed to low levels.

This method is conventionally called hydrogen water chemistry and is widely practiced for mitigating intergranular stress corrosion cracking of materials in boiling water reactors. When hydrogen water chemistry is practiced in a boiling water reactor, the electrochemical corrosion potential of the stainless steel material typically decreases from a positive value generally in the range of 0.050 to 0.200 V (SHE) under normal water chemistry to a value less than −0.230 V (SHE), where SHE stands for the standard hydrogen electrode. There is considerable evidence that when the electrochemical corrosion potential is below −0.230 V (SHE), intergranular stress corrosion cracking of materials such as stainless steel can be mitigated, and the initiation of intergranular stress corrosion cracking can be largely prevented.

Thus, considerable efforts have been made to develop reliable electrochemical corrosion potential sensors to be used as reference electrodes for determining the electrochemical corrosion potential of operating surfaces. These sensors are being used in boiling water reactors worldwide, with a high degree of success, which has enabled the determination of the minimum feedwater hydrogen injection rate required to achieve electrochemical corrosion potentials of reactor internal surfaces and piping below the desired negative value, −0.230 mV (SHE).

However, the sensors typically have a limited lifetime, in that some have failed after only a few months of use, while most have shown evidence of successful operation for approximately six to nine months. Only a few sensors have shown successful operation over a period of one fuel cycle, e.g. eighteen months in a US boiling water reactor.

Recent experience with boiling water reactors in the United States has shown that the two major modes of failure of the sensor have been cracking and corrosive attack in the ceramic-to-metal braze used at the sensor tip, and the dissolution of the sapphire insulating material used to electrically isolate the sensor tip from the metal conductor cable for platinum or stainless steel type sensors.

The electrochemical corrosion potential sensors may be mounted either directly in the reactor core region for directly monitoring electrochemical corrosion potential of in-core surfaces, or may be mounted outside the reactor core to monitor the electrochemical corrosion potential of out-of-core surfaces. However, the typical electrochemical corrosion potential sensor nevertheless experiences a severe operating environment in view of the high temperature of water, typically exceeding 288° C., relatively high flow rates, e.g up to several meters per second (m/s) or more, and the effects of high nuclear radiation in the core region. This environment complicates the design of the sensor, since suitable materials are required for this hostile environment, preferably configured to provide a water-tight assembly for a beneficial useful lifetime.

As indicated above, experience with the typical platinum electrochemical corrosion potential sensor has uncovered shortcomings leading to premature failure before expiration of a typical fuel cycle. Accordingly, it is desired to improve the design of electrochemical corrosion potential sensors to increase their useful life, e.g. to at least one fuel cycle.

SUMMARY

The invention relates to a sensor for a measuring an electrochemical corrosion potential comprising a sensor tip, a conductor electrically connected to the sensor tip, an insulating member which surrounds the conductor, a connecting member which surrounds the conductor, and a sleeve which fits over the sensor tip, the insulating member, and the connecting member, the sleeve having inner threads which engage with corresponding outer threads on at least one of the sensor tip and the connecting member.

The invention also relates to a method of making an electrochemical corrosion potential sensor comprising the steps of providing a sensor tip, connecting a conductor to the sensor tip, providing an insulating member around the conductor, providing a connecting member around the conductor, providing a sleeve which fits over the insulating member, a portion of the connecting member, and a portion of the sensor tip, forming inner threads on the sleeve, forming outer threads on at least one of the sensor tip and the connecting member, and engaging the inner threads with the outer threads.

The sensor sleeve can be preformed to have a high mechanical strength and high density, which provides excellent protection to the insulating member and braze joints of the sensor in the high temperature water environment. Exemplary embodiments of the sensor typically have a significantly increased lifetime which allows data on electrochemical corrosion potential to be acquired over a complete fuel cycle.

BRIEF DESCRIPTION OF THE DRAWINGS

Other features and advantages of the invention will be more readily understood upon reading the following detailed description, in conjunction with the drawings, in which.

DETAILED DESCRIPTION OF THE PREFERRED EMBODIMENTS

Figure 1:
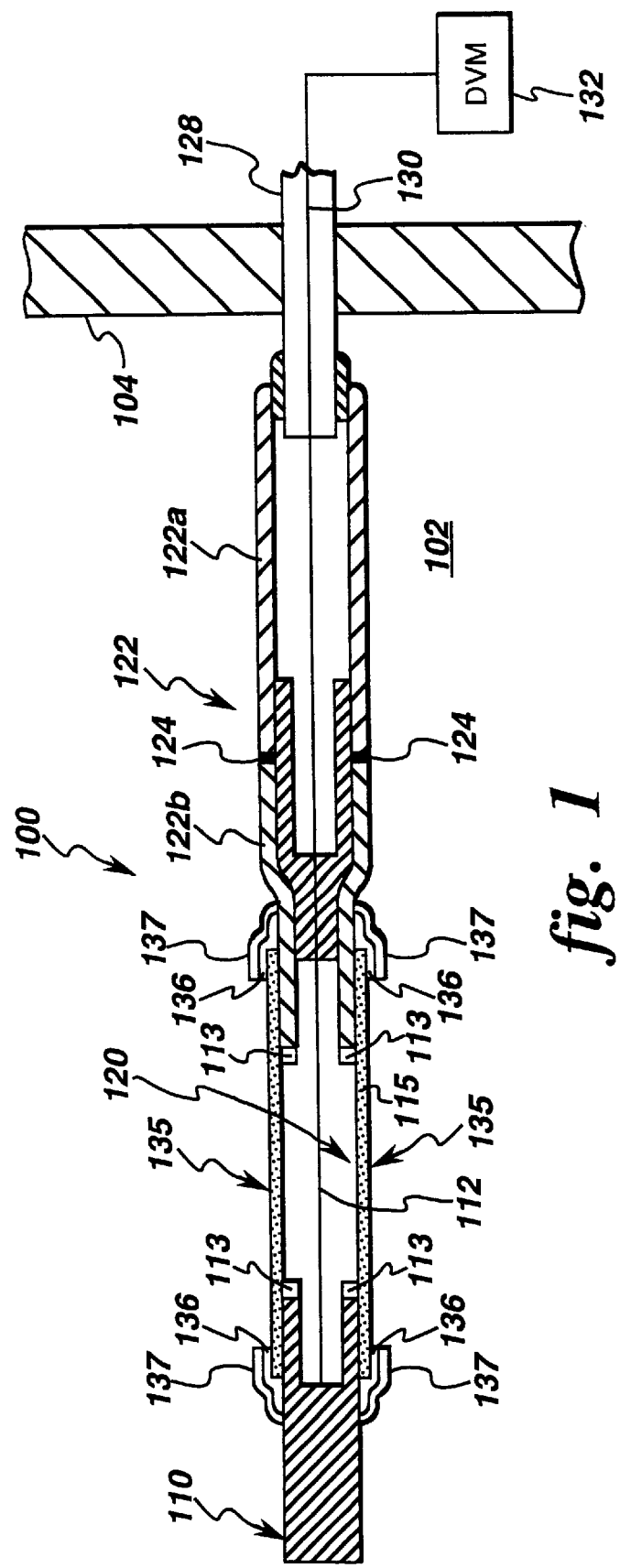
FIG. 1 is a drawing of an electrochemical corrosion potential sensor according to one embodiment of the invention.

Illustrated schematically in FIG. 1 is a sensor 100 configured for measuring the electrochemical corrosion potential of reactor surfaces in circulating water 102 inside a pressure vessel 104 of a conventional boiling water nuclear reactor, shown in relevant part. The sensor 100 includes a sensor tip 110 electrically connected to a central conductor 112. The sensor tip 110 may have any suitable configuration such as a cylindrical plug or tubular cup formed of stainless steel, for example, or of a noble metal such as platinum.

An electrical insulator 120, e.g. of ceramic, is joined at one end to the tip 110 around the conductor 112. A connecting member 122 is joined to the insulating member 120 at an end opposite the tip 110, also around the conductor 112, and is electrically insulated from the tip 110 by the insulating member 120.

In the exemplary embodiment illustrated in FIG. 1, the connecting member 122 includes a first portion 122a joined by a weld 124 to a second portion 122b to which the insulator 120 is directly attached. The first portion 122a may be formed of stainless steel, for example, and the second portion 122b may be formed of a conventional material such as Kovar, an iron-nickel-cobalt material, or from Invar also known as alloy 42, which is an iron-nickel material without cobalt for eliminating irradiation thereof during use in the boiling water reactor. The insulator 120 is typically formed of sapphire.

The sensor 100 is connected to a conducting cable 128 which electrically joins the sensor tip 110 to a conventional monitoring device such as a digital voltmeter (DVM) 132 for measuring the electrochemical corrosion potential in volts. The cable 128 includes a central conductor 130 which may be stainless steel spot welded to the tip conductor 112, and an outer electrically insulating sheath which may comprise a mineral oxide ceramic, for example.

In practice, a plurality of sensors are typically used in a boiling water reactor to measure electrochemical corrosion potential. The sensors are mounted in the boiling water reactor and may extend through a pressure vessel wall 104 for monitoring electrochemical corrosion potential of in-core surfaces in the water 102 circulating through the reactor core. The sensor 100 can therefore be subject to a high nuclear radiation environment, with elevated water temperatures, typically greater than 275° C., and with substantial water flow rates, e.g. in excess of 10 m/s.

The various components of the sensor 100 are typically sealed to prevent leakage of the water into the sensor 100. For example, the insulating member 120 is typically joined to the tip 110 and to the connecting member 122b at ceramic-to-metal braze joints 113. The brazing material may comprise, for example, a conventional silvercopper-titanium alloy, pure silver, or a silver-copper alloy. The braze joints 113 are formed by conventional brazing methods which typically occur at elevated temperatures such as about 940° C. In order to reduce the likelihood of undesirable cracking between the insulating member 120 and the tip 110 and connecting member 122b, the materials of these components preferably have coefficients of thermal expansion generally similar to that of the insulating member 120 for reducing differential thermal expansion and contraction during the brazing process. For the connecting member 122b, the Kovar or alloy 42 material provides this advantage; and for the sensor tip 110, platinum is typically used.

The insulating member 120 extends in part from both of its opposite ends into the tip 110 and the connecting member 122b, with a central exposed cylindrical surface 115 axially separating the tip 110 and connecting member 122b.

Due to the hostile environment of high radiation, high temperature water, and relatively high flow rates of water, one known failure mode of a sensor involves dissolution of the sapphire insulator which ablates away over time. According to an exemplary embodiment of the invention, the sensor 100 is provided with a sleeve which protects the sapphire insulating member 120 and prevents deterioration thereof. An example of the sleeve is shown in FIG. 1. The sleeve 135 covers the exposed surface 115 of the insulating member 120 and overlaps adjoining portions of the tip 110 and connecting member 122b to prevent dissolution of the insulating member 120 by the circulating water 102. The sleeve 135 typically has a thickness of about 0.38–0.64 mm (15–25 mil), for example, a length of about 0.63–1.27 cm (0.25–0.5 inches) and an inner diameter of about 0.38–0.43 cm (0.15–0.17 inches). These values are of course merely exemplary. The sleeve 135 preferably extends over the braze joints 113 for protection of the braze joints 113 and for providing a redundant seal. The sleeve 135 provides an effective barrier layer atop the otherwise exposed sapphire insulator 120. The sleeve typically comprises magnesia stabilized zirconia (MSZ), yttria stabilized zirconia (YSZ), or a zirconium alloy ("zircaloy") such as zircaloy-2 or zircaloy-4. These materials have a demonstrated ability to withstand the high temperature, high flow rate, radiation environment of nuclear reactors, based on in-reactor exposure experience.

The sleeve 135 may be formed by conventional methods. For example, the MSZ and YSZ sleeves may be formed by sintering a ceramic powder compact of the appropriate shape, e.g. in the shape of a cylindrical tube. The zircaloy sleeve may be formed by molding melted zircaloy into the appropriate shape, e.g. in the shape of a cylindrical tube. The sleeve 135 can also be made by forming a solid cylindrical block of MSZ, YSZ or zircaloy and boring a hole through the cylindrical block.

The sleeve 135 provides enhanced protection and lifetime to the sensor 100 due to its robust nature and sealing engagement with the sensor tip 110 and connecting member 122. For example, the process of preforming the sleeve by sintering or molding provides good mechanical strength and high density. The density of the sleeve 135 is typically greater than 97.5% of the theoretical density of the selected material, more typically greater than 98 or 99% of theoretical density, most typically greater than 99.95% of theoretical density.

After forming the sleeve 135 and sliding the sleeve on the sensor 100, the sleeve 135 can be further sealed in place over the insulating member 120 and portions of the sensor tip 110 and connecting member 122. According to a first embodiment shown in FIG. 1, after the sleeve 135 has been positioned on the insulating member 120, a suitable thickness of ceramic coating 137 is plasma sprayed over both ends of the sleeve 135 and a portion of the electrode tip 110 and connecting member 122b. The ceramic coating may comprise yttria stabilized zirconia (YSZ) or magnesia stabilized zirconia (MSZ), and may have a thickness of 0.5–1.0 mm, for example.

Typically, a bond coat 136 is applied, e.g. by plasma spraying, to each end of the sleeve 135 and to portions of the electrode tip 110 and connecting member 122b prior to applying the ceramic coating 137. The bond coat may comprise a material such as M-Chromium-Alumina-Yttrium alloy (MCrAlY alloy), where M=NiCoFe or Ni+Co. The bond coat 136 may have a thickness of about 0.125–0.25 mm, for example. The bond coat 136 and ceramic coating 137 together seal the sleeve 135 onto the remainder of the sensor 100. Sealing of the sleeve 135 prevents water from circulating around the sapphire insulating member 120 and causing it to deteriorate. The additional coating layers 136, 137 on both ends of the sleeve 135 and portions of the sensor tip 110 and connecting member 122b provide a barrier layer for preventing corrosion along the crevice formed between both ends of the sleeve 135 and the connecting member 122b and sensor tip 110.

Figure 2:
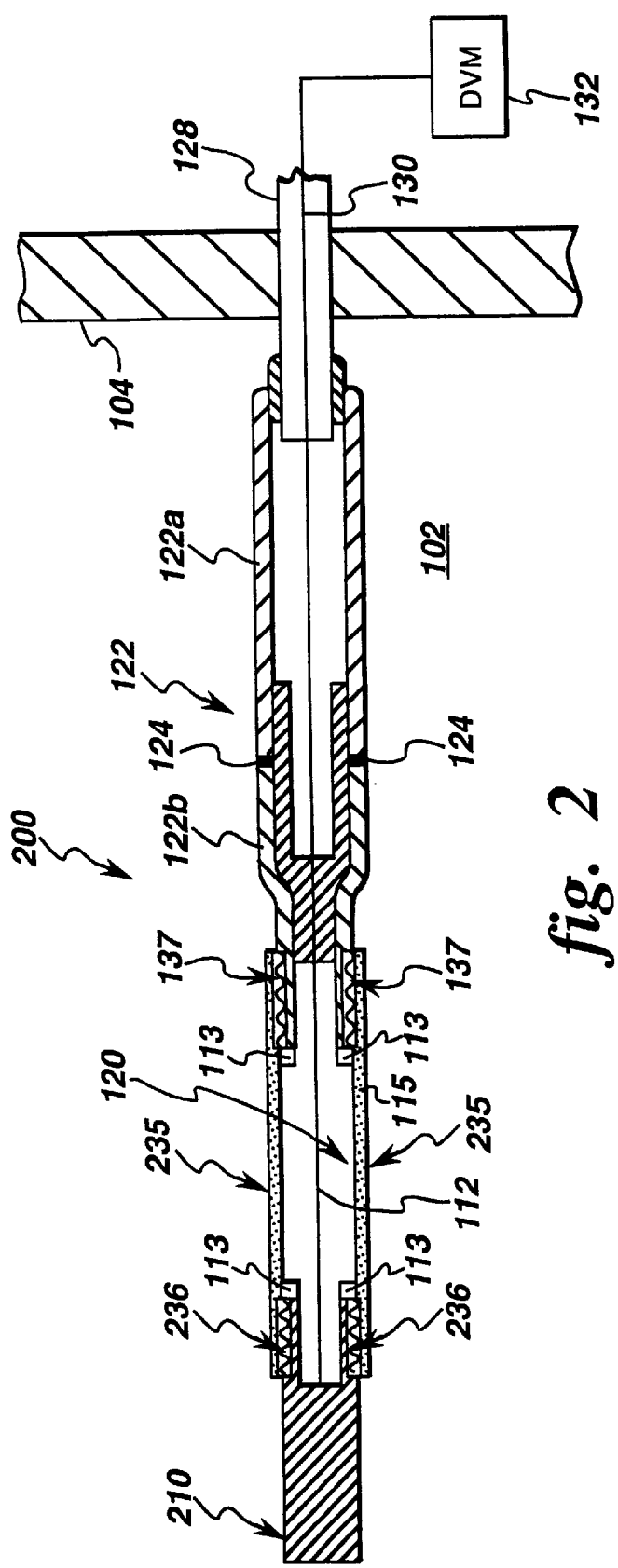
FIG. 2 is a drawing of an electrochemical corrosion potential sensor according to another embodiment of the invention.

According to a second embodiment of the invention, the sleeve is sealed onto the remainder of the sensor by threading it into adjacent components. As shown in FIG. 2, wherein like reference numbers refer to like components, threads 236, 237 are provided on the ends of the sleeve 235, on the sensor tip 210, and on the connecting member 222b. The sleeve 235 has inner threads which engage with corresponding outer threads on the sensor tip 210 and connecting member 222b. The connecting member 222b and the sensor tip 210 are typically threaded prior to applying the braze joints 113. The sleeve 235 can be screwed into the connecting member 222b to form a watertight seal. The sensor tip 210 can be screwed into the sleeve 235 to form a watertight seal.

Figure 3:
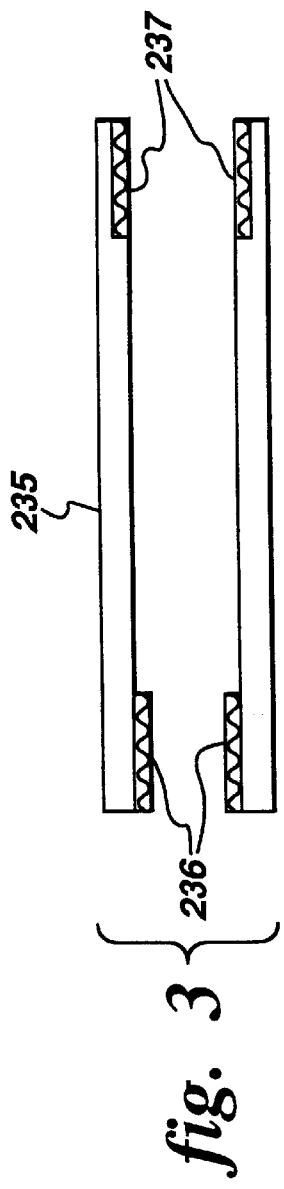
FIG. 3 is a drawing of the sleeve of FIG. 2.

As shown in FIG. 3, the threads 236 and 237 at opposite ends of the sleeve 235 may have different diameters. For example, the threads 237 may have a larger diameter than the threads 236. In this way, the insulating member 120 can be brazed to both the connecting member 222b and the sensor tip 210 first, and then the sleeve 235 can be slid over the sensor tip 210 and insulating member 120 and screwed into the connecting member 222b.

The threaded connection at 236 and 237 produces a good liquid seal to prevent water from reaching the insulator 120. Even if some water penetrates into a crevice between the sleeve and the sapphire, the sapphire will not typically experience high dissolution, because the water is stagnant. By contrast, high dissolution of sapphire has typically taken place in high flow rate water in laboratories and reactors. The sleeve can extend the lifetime of the sensor to beyond a fuel cycle and provide reliable readings of electrochemical corrosion potential in high temperature water. Accordingly, the electrochemical corrosion potential sensors having sleeves as illustrated in FIGS. 1 and 2 provide protection of the insulator 120 against dissolution in the high temperature and flow condition of the reactor water in a high radiation environment. This results in a corresponding increase in the useful life of the sensor.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

What is claimed is:

1. A method of making an electrochemical corrosion potential sensor electrode comprising the steps of:

provide a sensor tip;

connecting a conductor to the sensor tip;

providing an insulating member around the conductor;

providing a connecting member around the conductor;

providing a sleeve which fits over the insulating member, a portion of the connecting member, and a portion of the sensor tip;

forming inner threads on the sleeve;

forming outer threads on at least one of the sensor tip and the connecting member; and engaging the inner threads with the outer threads.

2. The method of claim 1, further comprising the step of forming the insulating member of sapphire.

3. The method of claim 2, further comprising the step of forming the connecting member of alloy 42.

4. The method of claim 3, further comprising the step of brazing the insulating member to at least one of the sensor tip and the connecting member.

* * * * *